(12) United States Patent
Acemoglu et al.

(10) Patent No.: US 8,536,346 B2
(45) Date of Patent: Sep. 17, 2013

(54) PROCESS OR MAKING N-HYDROXY-3[4-[[[2-(2METHYL-1H-INDOL-3-YL)ETHYL]AMINO]METHYL]PHENYL]-2E-2-PROPENAMIDE AND STARTING MATERIALS THEREFOR

(75) Inventors: Murat Acemoglu, Basel (CH); Joginder S. Bajwa, Elmwood Park, NJ (US); David John Parker, West Milford, NJ (US); Joel Slade, Flanders, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/243,001

(22) Filed: Sep. 23, 2011

(65) Prior Publication Data

US 2012/0010418 A1 Jan. 12, 2012

Related U.S. Application Data

(63) Continuation of application No. 12/302,572, filed as application No. PCT/US2007/070564 on Jun. 7, 2007, now abandoned.

(60) Provisional application No. 60/867,878, filed on Nov. 30, 2006, provisional application No. 60/804,527, filed on Jun. 12, 2006.

(51) Int. Cl.
*C07D 209/14* (2006.01)

(52) U.S. Cl.
USPC .......................................................... 548/495

(58) Field of Classification Search
USPC .......................................................... 548/495
See application file for complete search history.

(56) References Cited

FOREIGN PATENT DOCUMENTS

| EP | 0 233 413 | 8/1987 |
| GB | 146260 | 11/1976 |
| WO | 02/22577 | 3/2002 |
| WO | WO 02/055742 | 7/2002 |
| WO | WO 03/039599 | 5/2003 |
| WO | WO 2007146717 A2 | 12/2007 |

OTHER PUBLICATIONS

Slade, Joel et al: "Optimization and Scale-Up of the Grandberg Synthesis of 2-Methyltryptamine", Organic Process Research & Development, 11(4), 721-725 CODEN: OPRDFK; ISSN: 1083-6161, 2007.

Grandberg I.I. et al: "Indoles I. A New Method for the Synthesis of 2-Substituted Tryptamines", Chemistry of Heterocyclic Compounds, vol. 4, 1968, pp. 632-633.

The Chemical Society of Japan (ed.), The new course of Experimental Chemistry 14, Synthesis and Reaction of Organic Compound III, Maruzen Co., Ltd., Feb. 20, 1987, pp. 1380-1385 (English translation also attached).

*Primary Examiner* — Shawquia Young
(74) *Attorney, Agent, or Firm* — Matthew Mulkeen

(57) ABSTRACT

N-hydroxy-3-[4-[[[2-(2-methyl-1H-indol-3-yl)ethyl]amino]methyl]phenyl]-2E-2-propenamide and starting materials therefore are prepared by new synthetic methods.

7 Claims, No Drawings

PROCESS OR MAKING N-HYDROXY-3[4-[[[2-(2METHYL-1H-INDOL-3-YL)ETHYL]AMINO]METHYL]PHENYL]-2E-2-PROPENAMIDE AND STARTING MATERIALS THEREFOR

BACKGROUND OF THE INVENTION

This application is a continuation application of Ser. No. 12/302,572, filed Nov. 26, 2008, which is a National Phase application of PCT/US2007/070564, filed Jun. 7, 2007, which claims benefit of Provisional application No. 60/867,878, filed Nov. 30, 2008 and Provisional application No. 60/804,527, filed Jun. 12, 2006.

FIELD OF THE INVENTION

This invention relates to a process of making N-hydroxy-3-[4-[[[2-(2-methyl process for making n-hydroxy-3-[4-[[[2-(2-methyl-1h-indol-3-1H-indol-3-yl)ethyl]amino]methyl]phenyl]-2E-2-propenamide and starting materials therefore.

RELATED BACKGROUND ART

The compound N-hydroxy-3-[4-[[[2-(2-methyl-1H-indol-3-yl)ethyl]amino]methyl]phenyl]-2E-2-propenamide (alternatively, N-hydroxy-3-(4-{[2-(2-methyl-1H-indol-3-yl)-ethylamino]-methyl}-phenyl)-acrylamide) has the formula

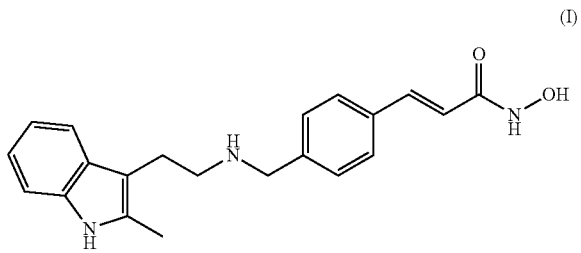 [SMILES: Cc1[nH]c2ccccc2c1CCNCc1ccc(/C=C/C(=O)NO)cc1]

(I)

as described in WO 02/22577. Valuable pharmacological properties are attributed to this compound; thus, it can be used, for example, as a histone deacetylase inhibitor useful in therapy for diseases which respond to inhibition of histone deacetylase activity. Previous attempts by the inventors to make this compound have had limited success due to the presence of various impurities and by-products in the reaction product; the removal of such impurities and by-products requires lengthy and tedious reworking/re-crystallization of the desired product. Thus, synthesis of N-hydroxy-3-[4-[[[2-(2-methyl-1H-indol-3-yl)ethyl]amino]methyl]phenyl]-2E-2-propenamide has heretofore been complicated, time-consuming and limited to small-scale synthesis.

SUMMARY OF THE INVENTION

The present invention is directed to a method of making N-hydroxy-3-[4-[[[2-(2-methyl-1H-indol-3-yl)ethyl]amino]methyl]phenyl]-2E-2-propenamide comprising the steps of: (a) combining sodium hydroxide and (E)-3-(4-{[2-(2-methyl-1H-indol-3-yl)-ethylamino]-methyl}-phenyl)-acrylic acid methyl ester hydrochloride salt to form an admixture at a temperature of less than about −10° C.; and subsequently (b) adding hydroxylamine to the admixture to form the N-hydroxy-3-[4-[[[2-(2-methyl-1H-indol-3-yl)ethyl]amino]methyl]phenyl]-2E-2-propenamide. The method further optionally comprises step (c) crystallizing the N-hydroxy-3-[4-[[[2-(2-methyl-1H-indol-3-yl)ethyl]amino]methyl]phenyl]-2E-2-propenamide. In a preferred embodiment of the invention, step (c) comprises the sub-steps of: (c1) heating the reaction mixture formed in step (b); (c2) stirring the reaction mixture; (c3) adding water to the reaction mixture; (c4) filtering the reaction mixture to provide a filtrate; (c5) adjusting the pH of the filtrate to a pH ranging from about 10 to about 11; (c6) adding seed crystals of N-hydroxy-3-[4-[[[2-(2-methyl-1H-indol-3-yl)ethyl]amino]methyl]phenyl]-2E-2-propenamide to the filtrate; (c7) stirring the filtrate until a suspension results; (c8) adjusting the pH of the suspension to a pH ranging from about 8.5 to about 9; and (c9) stirring the suspension. The method further optionally comprises step (d) isolating the N-hydroxy-3-[4-[[[2-(2-methyl-1H-indol-3-yl)ethyl]amino]methyl]phenyl]-2E-2-propenamide. In a preferred embodiment, step (d) comprises the sub-steps of: (d1) filtering the crystallized N-hydroxy-3-[4-[[[2-(2-methyl-1H-indol-3-yl)ethyl]amino]methyl]phenyl]-2E-2-propenamide from step (c); and (d2) drying the crystallized N-hydroxy-3-[4-[[[2-(2-methyl-1H-indol-3-yl)ethyl]amino]methyl]phenyl]-2E-2-propenamide.

The invention is further directed to a method of making (E)-3-(4-{[2-(2-methyl-1H-indol-3-yl)-ethylamino]-methyl]-phenyl)-acrylic acid methyl ester hydrochloride salt comprising the steps of: (a) combining 2-methyltryptamine and (E)-3-(4-formyl-phenyl)-acrylic acid methyl ester to form an admixture; (b) stirring the admixture for a time and at a temperature sufficient to form an imine intermediate; (c) reducing the imine intermediate to form the (E)-3-(4-{[2-(2-methyl-1H-indol-3-yl)-ethylamino]-methyl]-phenyl)-acrylic acid methyl ester and Addition of aqueous hydrochloric acid solution to the reaction mixture to form the hydrochloride salt. In a preferred embodiment of the invention, step (c) comprises the sub-steps of: (c1) cooling the admixture; (c2) adding sodium borohydride to the admixture; and (c3) combining the admixture with hydrochloric acid to crystallize/precipitate the (E)-3-(4-{[2-(2-methyl-1H-indol-3-yl)-ethylamino]-methyl]-phenyl)-acrylic acid methyl ester hydrochloride salt. In a further preferred embodiment, sub-step (c3) comprises the sub-steps of: (c3a) heating the admixture of sub-step (c2); (c3b) adding water to the admixture; and (c3c) adding hydrochloric acid to the admixture to crystallize (E)-3-(4-{[2-(2-methyl-1H-indol-3-yl)-ethylamino]-methyl]-phenyl)-acrylic acid methyl ester hydrochloride salt. The method further optionally comprises step (d) heating and cooling the suspension of (E)-3-(4-{[2-(2-methyl-1H-indol-3-yl)-ethylamino]-methyl]-phenyl)-acrylic acid methyl ester hydrochloride salt to decompose residual amine-boron complexes in the reaction mixture. In a preferred embodiment of the invention, step (d) comprises the sub-steps of: (d1) heating the suspension formed when the hydrochloride salt is formed in step (c); (d2) stirring the suspension at the temperature of sub-step (d1); (d3) cooling the suspension; and (d4) stirring the suspension at the temperature of sub-step (d3). The method further optionally comprises step (e) isolating (E)-3-(4-{[2-(2-methyl-1H-indol-3-yl)-ethylamino]-methyl]-phenyl)-acrylic acid methyl ester hydrochloride salt. In a preferred embodiment, step (e) comprises the sub-steps of: (e1) filtering the suspension of step (d); and (e2) drying the (E)-3-(4-{[2-(2-methyl-1H-indol-3-yl)-ethylamino]-methyl]-phenyl)-acrylic acid methyl ester hydrochloride salt.

The present invention is further directed to a method of making 2-methyltryptamine comprising the steps of: (a) providing an admixture of phenylhydrazine and 5-chloro-2-pentanone in ethanol at a first temperature; (b) adding ethanol to the admixture and refluxing the mixture; (c) distilling ethanol; (d) adding water to the residual solution; (e) cooling the residual solution to form 2-methyltryptamine. In a preferred embodiment of the present invention, the method further comprises the step of (f) isolating and purifying the 2-methyltryptamine. In more preferred embodiments of the present invention, step (f) includes the sub-steps of: (f1) washing the residual solution with toluene; (f2) isolating the 2-methyltryptamine; (f3) washing the 2-methyltryptamine with toluene; and (f4) drying the 2-methyltryptamine.

DETAILED DESCRIPTION OF THE INVENTION

The present invention is directed to a method of making N-hydroxy-3-[4-[[[2-(2-methyl-1H-indol-3-yl)ethyl]amino]methyl]phenyl]-2E-2-propenamide comprising the steps of: (a) combining (E)-3-(4-{[2-(2-methyl-1H-indol-3-yl)-ethyl]amino]-methyl]-phenyl)-acrylic acid methyl ester hydrochloride salt and sodium hydroxide to form an admixture at a temperature of less than about −10° C.; and subsequently (b) adding hydroxylamine to the admixture to form the N-hydroxy-3-[4-[[[2-(2-methyl-1H-indol-3-yl)ethyl]amino]methyl]phenyl]-2E-2-propenamide as shown below:

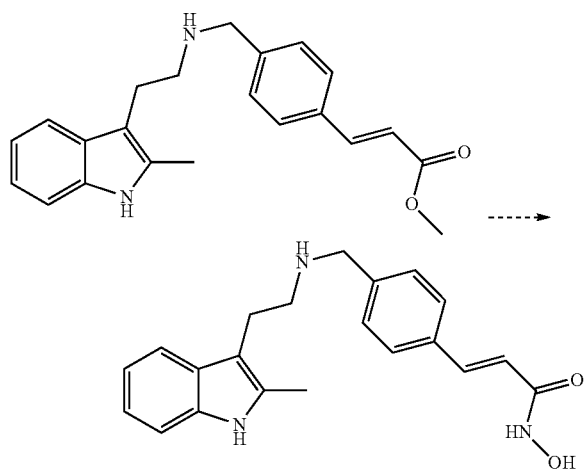

Additionally, the inventive method may comprise the steps of crystallizing and isolating the N-hydroxy-3-[4-[[[2-(2-methyl-1H-indol-3-yl)ethyl]amino]methyl]phenyl]-2E-2-propenamide. The inventive method does not require time-consuming, complicated reworking/re-crystallization of reaction product steps. In other words, the inventive method allows for the yield of N-hydroxy-3-[4-[[[2-(2-methyl-1H-indol-3-yl) ethyl]amino]methyl]phenyl]-2E-2-propenamide in one single process step in high yield and sufficient quality.

In the first step of the method of the first embodiment, (E)-3-(4-{[2-(2-methyl-1H-indol-3-yl)-ethylamino]-methyl]-phenyl)-acrylic acid methyl ester hydrochloride salt and sodium hydroxide are combined at a temperature of less than about −10° C. to form an admixture. More preferably, the temperature is less than about −15° C. In one embodiment, the temperature is about 0° C. The temperature can be achieved and maintained via any suitable means. Likewise, the admixture can be made in any suitable vessel which must be free of iron and heavy metals wherein the reaction is performed under an inert atmosphere. Heavy metals and iron (metallic Fe and its salts) would catalyse the decomposition of hydroxylamine Typically, the (E)-3-(4-{[2-(2-methyl-1H-indol-3-yl)-ethyl]amino]-methyl]-phenyl)-acrylic acid methyl ester hydrochloride salt (alternatively known as 3-(4-{[2-(2-methyl-1H-indol-3-yl)-ethylamino]-methyl}-phenyl)-(2E)-2-propenoic acid methyl ester is provided in the form of a suspension in methanol. Preferably, the (E)-3-(4-{[2-(2-methyl-1H-indol-3-yl)-ethyl]amino]-methyl]phenyl)-acrylic acid methyl ester hydrochloride salt is placed in a suitable reaction vessel to which methanol is added, and the resulting suspension is then cooled to a temperature of less than about −10° C. (E)-3-(4-{[2-(2-methyl-1H-indol-3-yl)-ethylamino]-methyl]-phenyl)-acrylic acid methyl ester hydrochloride salt can be prepared according to the method of the second embodiment of this invention. (E)-3-(4-{[2-(2-methyl-1H-indol-3-yl)-ethylamino]-methyl]-phenyl)-acrylic acid methyl ester hydrochloride salt is preferably defined as 1.0 equivalent. Typically, the sodium hydroxide is provided in the form of a solution, preferably in methanol. Sodium hydroxide is a commercially available starting material. Sodium hydroxide is preferably used in an amount ranging from about 2.5 to about 3.5 equivalents.

Preferably a methanol solution of sodium hydroxide is added to a suspension of (E)-3-(4-{[2-(2-methyl-1H-indol-3-yl)-ethylamino]-methyl]-phenyl)-acrylic acid methyl ester hydrochloride salt in a suitable reaction vessel over a period of time. More preferably, the sodium hydroxide solution is added over a period of time of about 20-40 minutes, preferably 30 minutes, while maintaining the temperature of less than about −10° C.

In the second step of the method of the first embodiment, hydroxylamine is added to the admixture from the first step to form the N-hydroxy-3-[4-[[[2-(2-methyl-1H-indol-3-yl) ethyl]amino]methyl]phenyl]-2E-2-propenamide. The temperature of the first step, i.e., less than about −10° C., is maintained during this step.

Typically the hydroxylamine is supplied in the form of a solution in water.

Hydroxylamine is a commercially available starting material. Hydroxylamine is preferably used in an amount ranging from about 4 to about 13 equivalents. Preferably an aqueous solution of hydroxylamine, e.g., a 50% in water solution, is added to the admixture of (E)-3-(4-{[2-(2-methyl-1H-indol-3-yl)-ethylamino]-methyl]-phenyl)-acrylic acid methyl ester hydrochloride salt and sodium hydroxide in a suitable reaction vessel over a period of time. More preferably, the hydroxylamine solution is added over a period of time of about 20-24 minutes, preferably about 30 minutes, while maintaining the temperature of less than about −10° C. In the course of conducting step (b), caution should be taken to add the hydroxylamine to the admixture in such a manner as to avoid contact with any apparatus or vessel used for the sodium hydroxide in step (a), e.g., the same addition funnel should not be used; in other words, reaction between hydroxylamine and sodium hydroxide should be avoided prior to adding the hydroxylamine to the admixture. In addition, all vessels and pipelines used for the addition of hydroxylamine must be free of iron and heavy metals.

In a preferred embodiment of the present invention, the mixture is stirred at the temperature of step (a) until the reaction is complete or nearly complete; typically, completion of the reaction takes about 7 hours. Completion of the reaction can be monitored by HPLC; in one preferred embodiment, a conversion of >99.5% is seen.

The method of the first embodiment may further comprise the step of (c) crystallizing the N-hydroxy-3-[4-[[[2-(2-methyl-1H-indol-3-yl)ethyl]amino]methyl]phenyl]-2E-2-propenamide. In a preferred embodiment of the present invention, such a step may include any or all of the sub-steps of: (c1) heating the reaction mixture formed in step (b); (c2)

stirring the reaction mixture; (c3) adding water to the reaction mixture; (c4) filtering the reaction mixture to provide a filtrate; (c5) adjusting the pH of the filtrate to a pH ranging from about 10 to about 11; (c6) adding seed crystals of N-hydroxy-3-[4-[[[2-(2-methyl-1H-indol-3-yl)ethyl]amino]methyl]phenyl]-2E-2-propenamide to the filtrate; (c7) stirring the filtrate until a suspension results; (c8) adjusting the pH of the suspension to a pH ranging from about 8.5 to about 9; and (c9) stirring the suspension. Preferably all of steps (c1) to (c9) are conducted at the temperature achieved by the heating of step (c1).

In step (c1), the reaction mixture is formed when the hydroxylamine is added to the admixture of the methyl ester and the sodium hydroxide. Preferably the reaction mixture is heated to a temperature ranging from about 0° C. to about 25° C. Heating can be accomplished by any suitable means. In step (c2), the reaction mixture is stirred at the temperature achieved by the heating of step (c1). Preferably the reaction mixture is stirred for a period of time of about 13 hours. In one preferred embodiment of the present invention, steps (c1) and (c2) are repeated to achieve gradual heating, i.e., the reaction mixture is first heated to a temperature ranging from about 0° C. to about 5° C. and stirred for about 4-6 hours, preferably 5 hours and then heated to a temperature ranging from about 20° C. to about 25° C. and stirred for an additional about 8-16 hours.

In step (c3), water is added to the reaction mixture. Typically, demineralized water is added over a period of time, more preferably over a period of about 30 minutes at a temperature between about 20-25° C., to achieve a solution.

In step (c4), the reaction mixture is filtered to provide a filtrate. Filtration can be accomplished using any suitable means or filter medium;

Step (c4) also optionally comprises the sub-step of washing the filtering medium and adding the wash to the filtrate obtained.

In step (c5), the pH of the filtrate is adjusted to a pH ranging from about 10 to about 11, more preferably from about 10.3 to about 10.7. Addition of aqueous hydrochloric acid is typically used for this purpose.

In step (c6), seed crystals of N-hydroxy-3-[4-[[[2-(2-methyl-1H-indol-3-yl)ethyl]amino]methyl]phenyl]-2E-2-propenamide are added to the filtrate. This is typically accomplished by the introduction of an aqueous suspension of N-hydroxy-3-[4-[[[2-(2-methyl-1H-indol-3-yl)ethyl]amino]methyl]phenyl]-2E-2-propenamide crystals.

In step (c7), the filtrate is stirred until a suspension results. Preferably the filtrate is stirred for a period of about 30 minutes to several hours, until crystallization becomes evident and visible.

In step (c8), the pH of the suspension is adjusted to a pH ranging from about 8.5 to about 9. Addition of aqueous hydrochloric acid is typically used for this purpose.

In step (c9), the suspension is stirred until the N-hydroxy-3-[4-[[[2-(2-methyl-1H-indol-3-yl)ethyl]amino]methyl]phenyl]-2E-2-propenamide crystallizes. Preferably the suspension is stirred for a period of about 30 minutes to several hours until the reaction is complete. The method of the first embodiment may further comprise the step of (d) isolating the N-hydroxy-3-[4-[[[2-(2-methyl-1H-indol-3-yl)ethyl]amino]methyl]phenyl]-2E-2-propenamide. In a preferred embodiment of the present invention, such a step may include any or all of the sub-steps of: (d1) filtering the crystallized N-hydroxy-3-[4-[[[2-(2-methyl-1H-indol-3-yl)ethyl]amino]methyl]phenyl]-2E-2-propenamide from step (c); and (d2) drying the crystallized N-hydroxy-3-[4-[[[2-(2-methyl-1H-indol-3-yl)ethyl]amino]methyl]phenyl]-2E-2-propenamide.

In step (d1), the crystallized N-hydroxy-3-[4-[[[2-(2-methyl-1H-indol-3-yl)ethyl]amino]methyl]phenyl]-2E-2-propenamide is filtered. Filtration can be accomplished using any suitable means. Typically the filter cake is washed with, e.g., a 1:1 mixture of de-mineralized water and methanol.

In step (d2), the crystallized N-hydroxy-3-[4-[[[2-(2-methyl-1H-indol-3-yl)ethyl]amino]methyl]phenyl]-2E-2-propenamide is dried. Drying can be accomplished by any suitable means. Drying at 45-50° C./1-5 mbar for about 24 hours was usually sufficient.

The second embodiment of the present invention is directed to a method of making (E)-3-(4-{[2-(2-methyl-1H-indol-3-yl)-ethylamino]-methyl}-phenyl)-acrylic acid methyl ester hydrochloride salt, one of the starting materials used in the synthesis of N-hydroxy-3-[4-[[[2-(2-methyl-1H-indol-3-yl)ethyl]amino]methyl]phenyl]-2E-2-propenamide in the first embodiment. In particular, the second embodiment of the present invention is directed to a method of making (E)-3-(4-{[2-(2-methyl-1H-indol-3-yl)-ethylamino]-methyl]-phenyl)-acrylic acid methyl ester hydrochloride salt comprising the steps of: (a) combining 2-methyltryptamine and (E)-3-(4-formyl-phenyl)-acrylic acid methyl ester to form an admixture; (b) stirring the admixture for a time and at a temperature sufficient to form an imine intermediate; and (c) reducing the imine intermediate to form the (E)-3-(4-{[2-(2-methyl-1H-indol-3-yl)-ethylamino]-methyl]-phenyl)-acrylic acid methyl ester hydrochloride salt.

In the first step of the method of the second embodiment, 2-methyl tryptamine and (E)-3-(4-formyl-phenyl)-acrylic acid methyl ester are combined to form an admixture. Preferably the temperature ranges from about 20° C. to about 25° C. The admixture can be made in any suitable vessel. Typically both the 2-methyltryptamine and the (E)-3-(4-formyl-phenyl)-acrylic acid methyl ester are dissolved in a solvent, e.g., methanol, to accomplish admixture.

2-Methyltryptamine is made according to known syntheses or made according to the method of the third embodiment of the invention below. 2-Methyltryptamine is preferably used in an amount ranging from about 0.9 to about 1.0 equivalents. (E)-3-(4-formyl-phenyl)-acrylic acid methyl ester can be purchased from a commercial source or made according to known syntheses. (E)-3-(4-formyl-phenyl)-acrylic acid methyl ester is preferably used in an amount ranging from about 1.0 to about 1.1 equivalents.

In the second step, the admixture of 2-methyltryptamine and (E)-3-(4-formyl-phenyl)-acrylic acid methyl ester is stirred for a time and at a temperature sufficient to produce the imine intermediate

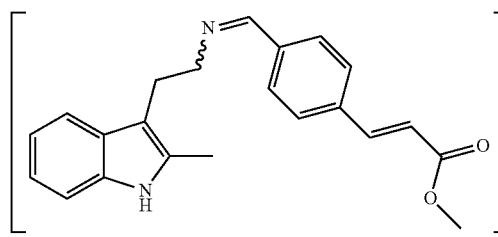

Preferably the admixture is stirred for about 1 hour at a temperature ranging from about 20 to about 25° C. In step (c) of the method of the second embodiment, the imine intermediate is reduced with sodium borohydride to form the (E)-3-(4-{[2-(2-methyl-1H-indol-3-yl)-ethylamino]-methyl]-phenyl)-acrylic acid methyl ester, which is subsequently crystallized/precipitated as hydrochloride salt. In a preferred embodiment of the invention, step (c) comprises the sub-steps of: (c1) cooling the admixture; (c2) adding sodium borohydride to the admixture; and (c3) combining the admixture with hydrochloric acid to crystallize/precipitate the (E)-3-(4-{[2-(2-methyl-1H-indol-3-yl)-ethylamino]-methyl]-phenyl)-acrylic acid methyl ester hydrochloride salt.

In one embodiment of the invention, the admixture is diluted with solvent, e.g., methanol, prior to sub-step (c1). The cooling of sub-step (c1) can be accomplished by any known means, e.g., ice bath, cooling jacket, etc. Preferably the admixture is cooled to a temperature of about −10 to −20° C., preferably −15° C.

The addition of the sodium borohydride in sub-step (c2) is preferably accomplished in portions over a period of time while maintaining the temperature of sub-step (c1). More preferably, the time for addition is about 1 hour and the temperature maintained ranges from about −15° C. to about −10° C. Preferably the sodium borohydride is added in solid form and in an amount ranging from about 0.4 to about 0.7 equivalents.

In sub-step (c3), the admixture is combined with an acid, e.g. hydrochloric acid to precipitate the (E)-3-(4-{[2-(2-methyl-1H-indol-3-yl)-ethylamino]-methyl]phenyl)-acrylic acid methyl ester hydrochloride salt. Preferably this sub-step is carried out after a period of stirring the admixture of sub-step (c2). Combination with the hydrochloric acid can be accomplished in accordance with this invention in several ways. One preferred manner comprises the slow addition of the admixture to pre-cooled aqueous hydrochloric acid solution; typically the hydrochloric acid solution is cooled to a temperature of about 0° C. to about 5° C.

Another preferred manner of combining with hydrochloric acid comprises the sub-steps of: (c3a) heating the admixture of sub-step (c2); (c3b) adding water to the admixture; and (c3c) adding hydrochloric acid to the admixture to precipitate (E)-3-(4-{[2-(2-methyl-1H-indol-3-yl)-ethylamino]-methyl]phenyl)-acrylic acid methyl ester hydrochloride salt. In sub-step (c3a), the admixture is heated to a temperature ranging from about 20° C. to about 25° C. over a period of time of about 20-45 minutes, preferably about 25 minutes. In sub-step (c3b), water is added slowly, preferably after a period of stirring the admixture of sub-step (c3a). In sub-step (c3c), preferably the hydrochloric acid is aqueous and added slowly in portion. Preferably, the first portion of the hydrochloric acid is as much as needed to adjust the pH of the reaction mixture to 8.5. The hydrochloric acid solution is added such that the temperature is maintained at 20-25° C. Subsequently, the reaction mixture is stirred at this temperature for at least one hour to allow crystallization of the product, before more hydrochloric acid can be added.

The method of the second embodiment may also comprise the step of (d) heating and cooling the suspension of (E)-3-(4-{[2-(2-methyl-1H-indol-3-yl)-ethylamino]-methyl]-phenyl)-acrylic acid methyl ester hydrochloride salt to improve quality and increase filterability. In a preferred embodiment, such a step may include any or all of the sub-steps of: (d1) heating the suspension formed when the imine intermediate is reduced and hydrochloric acid is added to form the hydrochloride in step (c); (d2) stirring the suspension at the temperature of sub-step (d1); (d3) cooling the suspension; and (d4) stirring the suspension at the temperature of sub-step (d3). Preferably the temperature of sub-step (d1) ranges from about 60° C. to about 65° C., and heating is accomplished over a period of time ranging from about 30 minutes to about 45 minutes. Preferably the stirring of sub-step (d2) is carried out for a period of time ranging from about 5 minutes to about 30 minutes. Preferably the temperature of sub-step (d3) ranges from about −15° C. to about −10° C. and is accomplished over a period of time ranging from about 45 minutes to about 1 hour. Preferably the stirring of sub-step (d4) is carried out for a period of time ranging from about 30 minutes to about several hours. In a particularly preferred embodiment of this invention, all of sub-steps (d1) through (d4) are repeated one or more times; in effect, the temperature of the precipitate is oscillated between −15° C. and 65° C. before filtration of the product.

The method of the second embodiment of the invention may also comprise the step of (e) isolating (E)-3-(4-{[2-(2-methyl-1H-indol-3-yl)-ethylamino]-methyl]-phenyl)-acrylic acid methyl ester hydrochloride salt. In a preferred embodiment, such a step may include any or all of the sub-steps of: (e1) filtering the suspension of step (d); and (e2) drying the (E)-3-(4-{[2-(2-methyl-1H-indol-3-yl)-ethylamino]-methyl]-phenyl)-acrylic acid methyl ester hydrochloride salt.

In step (e1), the suspension of crystallized (E)-3-(4-{[2-(2-methyl-1H-indol-3-yl)-ethylamino]-methyl]-phenyl)-acrylic acid methyl ester hydrochloride salt from step (d) is filtered. Filtration can be accomplished using any suitable means. Typically the filter cake is washed with, e.g., a pre-cooled (about −10° C.) mixture of de-mineralized water and methanol or pre-cooled (about −15° C.) methanol.

In step (e2), the crystallized (E)-3-(4-{[2-(2-methyl-1H-indol-3-yl)-ethylamino]-methyl]-phenyl)-acrylic acid methyl ester hydrochloride salt is dried. Drying can be accomplished by any suitable means. Drying at 50° C. at reduced pressure is particularly preferred.

The third embodiment of the present invention is directed to a method of making a starting material useful in the synthesis of (E)-3-(4-{[2-(2-methyl-1H-indol-3-yl)-ethylamino]-methyl]-phenyl)-acrylic acid methyl ester hydrochloride salt. In particular, the third embodiment of the present invention is directed to a method of making 2-methyltryptamine comprising the steps of: (a) providing an admixture of phenylhydrazine and 5-chloro-2-pentanone in ethanol at a first temperature; (b) adding ethanol to the admixture and refluxing the mixture; (c) distilling ethanol; (d) adding water to the residual solution; (e) cooling the residual solution to form 2-methyltryptamine.

In the first step of the method of the third embodiment, an admixture of phenylhydrazine and 5-chloro-2-pentanone is provided in ethanol at a first temperature. Phenylhydrazine, 5-chloro-2-pentanone and ethanol are commercially available starting materials. For purposes of this invention, it is preferred to use equimolar amounts of phenylhydrazine and 5-chloro-2-pentanone. Thus, phenylhydrazine is preferably used in an amount ranging from about 0.5 to about 1.5, and 5-chloro-2-pentanone is preferably used in an amount ranging from about 1 to about 2. In a preferred embodiment of the present invention, step (a) comprises the sub-steps: (a1) providing a solution of phenylhydrazine in ethanol; (a2) warming the solution to a temperature ranging from about 30° C. to about 40° C., more preferably a temperature of about 30-40° C.; (a3) holding the reaction at a temperature ranging from about 35° C. to about 45° C., while 5-chloro-2-pentanone is added to the reaction mixture, typically over a period of time of about 15-45 minutes; and (a4) holding the reaction for a period of about 30-60 minutes] at the temperature of step (a3). In this step, careful control of the temperature and time parameters is important in terms of controlling impurities.

In the second step of the method of the third embodiment, ethanol is added to the admixture and the mixture is refluxed. Ethanol is preferably added in an amount ranging from about 10 to about 20 parts. Typically, the reaction mixture is immediately warmed to reflux and held for 50-60 minutes minimum. After reflux, the reaction mixture is typically cooled to room temperature over a period of about 20 minutes.

In the third step of the method of the third embodiment, ethanol is distilled. Distillation can be accomplished using any suitable means; vacuum distillation is particularly preferred for this purpose. Partial distillation of ethanol is typically conducted by measuring the volume in the flask.

In the fourth step of the method of the third embodiment, water is added to the residual solution. Water is preferably added in an amount ranging from about 10 to about 20 parts. In a typical process, distillation is continued at the same conditions by removing ethanol and then additional water is added to the residual mixture. Water is preferably added in an amount ranging from about 10 to about 20 parts.

In the fifth step of the method of the third embodiment, the residual solution is cooled to form 2-methyltryptamine. Typically, the residual solution is cooled to a temperature of less than about 25° C.

The method of the third embodiment may further comprise the step of (f) isolating and purifying the 2-methyltryptamine. In preferred embodiments of the present invention, step (f) includes the sub-steps of: (f1) washing the residual solution with toluene; (f2) isolating the 2-methyltryptamine; (f3) washing the 2-methyltryptamine with toluene; and (f4) drying the 2-methyltryptamine.

In step (f1), the residual solution is washed with toluene. In step (f2), the 2-methyltryptamine is isolated. Isolation can be accomplished by any suitable means. In step (f3), the 2-methyltryptamine is washed with toluene, preferably cold toluene, i.e., ≦0° C. In step (f4), the 2-methyltryptamine is dried. Drying can be accomplished by any suitable means. Drying under vacuum at 45° C. until an LOD of <1% is obtained is particularly preferred.

The method of the third embodiment can be used to produce 2-methyltryptamine which is a starting material in the synthesis of (E)-3-(4-{[2-(2-methyl-1H-indol-3-yl)-ethylamino]-methyl]-phenyl)-acrylic acid methyl ester hydrochloride salt.

Specific embodiments of the invention will now be demonstrated by reference to the following examples. It should be understood that these examples are disclosed solely by way of illustrating the invention and should not be taken in any way to limit the scope of the present invention.

Example 1

Preparation of N-hydroxy-3-[4-[[[2-(2-methyl-1H-indol-3-yl)ethyl]amino]methyl]phenyl]-2E-2-propenamide (E)-3-(4-{[2-(2-methyl-1H-indol-3-yl)-ethylamino]-methyl]phenyl)-acrylic acid methyl ester hydrochloride salt (90 g, 233.8 mmole) is placed in a 4-necked reaction flask and methanol (475 g) is added. The suspension is cooled to −15° C. A solution of sodium hydroxide (28.2 g, 705 mmole) in methanol (419.2 g) is added to the suspension at −15° C. (addition time ca. 30 minutes), followed by the addition of the hydroxylamine solution (100.3 g of a 50% solution in water, corresponding to 50.15 g hydroxylamine, 1518 mmole) at, this temperature (addition time ca. 30 minutes). Caution: it is important to use different addition funnels for the sodium hydroxide and hydroxylamine solutions respectively. Stirring is continued at −15° C. for an additional 7 hours until a conversion of >99.5 area % is achieved according to HPLC. The reaction mixture is warmed to 0° C., stirred for 5 hours at 0-5° C., warmed to 20° C. and stirring is continued for 8 hours at 20-25° C. De-mineralized water (225 g) is added to the suspension at 20-25° C. during 30 minutes to obtain a solution. The solution is filtered and the filter as well as the filter pipeline are washed with de-mineralized water (225 g). The pH of the solution is adjusted to 10.3-10.7 by the addition of an aqueous hydrochloric acid solution (ca. 140 g of a 7.8 m/m % solution in water). Seed crystals are added as a suspension of N-hydroxy-3-[4-[[[2-(2-methyl-1H-indol-3-yl)ethyl]amino]methyl]phenyl]-2E-2-propenamide free base (80 mg) in water (5 g) and the mixture is stirred for ca. 30 minutes at 20-25° C., until a suspension is formed. The pH of the suspension is then adjusted to 8.5-9.0 by addition of an aqueous hydrochloric acid solution (ca. 108 g of a 7.8 m/m % solution in de-mineralized water) at 20-25° C. and stirring is continued for at least 30 minutes at 20-25° C. The solid product is isolated by filtration and the filter cake is washed with a 1:1 (v/v) mixture of demineralized water and methanol (140 mL). The wet product is dried at 45-50° C./5 mbar for 24 hours to obtain N-hydroxy-3-[4-[[[2-(2-methyl-1H-indol-3-yl)ethyl]amino]methyl]phenyl]-2E-2-propenamide. Yield: 81.15 g; 99.3% of the theory. HPLC analysis indicated 97.6 area % purity for the product, which comprised 3.2% w/w of water. The hydroxylamine content was found to be 345 ppm, which is sufficient for the preparation of the corresponding lactate salt with <5 ppm hydroxylamine.

Example 2

Preparation of (E)-3-(4-{[2-(2-methyl-1H-indol-3-yl)-ethylamino]-methyl]-phenyl)-Acrylic Acid Methyl Ester Hydrochloride Salt 2-Methyltryptamine (100 g, 573.8 mmole) and (E)-3-(4-formyl-phenyl)-acrylic acid methyl ester (115 g, 604.6 mmole) are dissolved in methanol (1250 mL). The solution is stirred for 1 hour at 20-25° C., to allow the formation of the imine intermediate. The solution is diluted with methanol (1250 mL) and cooled to −15° C. Sodium borohydride (16.25 g, 429.5 mmole) is added in several portions during ca. 1 hour while maintaining the temperature at −15° C. to −10° C. The reaction mixture is stirred for additional 30 minutes at this temperature and the reaction is quenched by slow addition of the reaction mixture onto a pre-cooled solution of hydrochloric acid (488 g concentrated hydrochloric acid in 337 g of water and 198 g of methanol) at 0-5° C. A suspension is formed. The addition funnel is rinsed with methanol (40 g) and the temperature is raised to 60-65° C. within 1 hour. The suspension is stirred for 1 hour at 60-65° C. and the temperature is lowered to −15° C. within 1 hour. The suspension is stirred for 1, hour at −15° C. to −10° C. and the product is isolated by filtration. The wet filter cake is washed in several portions with a pre-cooled mixture (−10° C.) of water (300 mL) and methanol (600 mL). The wet product is dried at 50° C. under reduced pressure to obtain (E)-3-(4-{[2-(2-methyl-1H-indol-3-yl)-ethylamino]-methyl]-phenyl)-acrylic acid methyl ester hydrochloride salt as product. The product has usually >99 area % purity according to HPLC. IR, NMR and HR-MS confirmed the proposed structure. Melting point: decomposition starting at 251-252° C.

Example 3

Preparation of (E)-3-(4-{[2-(2-methyl-1H-indol-3-yl)-ethylamino]-methyl]-phenyl)-Acrylic Acid methyl Ester Hydrochloride Salt 2-Methyltryptamine (50 g, 287 mmole) and (E)-3-(4-formyl-phenyl)-acrylic acid methyl ester (54.6 g, 287 mmole)

are suspended in methanol (514 g). The solution is stirred for 1 hour at 20-25° C., to allow the formation of the imine intermediate. The solution is cooled to −15° C. within ca. 20 minutes. Sodium borohydride (5.43 g, 143.5 mmole) is added in several portions during ca. 1 hour while maintaining the temperature at −15° C. to −10° C. The reaction mixture is stirred for additional 30 minutes at this temperature and the temperature is raised to 20-25° C. within ca. 25 minutes. The reaction mixture is stirred for 30 minutes at 20-25° C. and water (80 g) is slowly added while maintaining the temperature at 20-25° C. An aqueous solution of hydrochloric acid (70.5 g concentrated HCl in 50 g of water) is slowly added to the reaction mixture such that the temperature is maintained at 20-25° C. and the hydrogen gas evolution can be controlled. The addition needs ca. 1 hour in this case. A second portion of aqueous hydrochloric acid solution (70.5 g concentrated HCl in 50 g water) is added within 30 minutes and the temperature is raised to 65° C. within 30 minutes. The suspension is stirred for 30 minutes at 65° C. and the temperature is lowered to −15° C. within 45 minutes. After 10 minutes stirring at −15° C., the temperature is raised again to 65° C. and the suspension is stirred for 30 minutes at this temperature. Finally, the suspension is cooled to −15° C. within 45 minutes and stirring is continued for additional 30 minutes at this temperature. The product is isolated by filtration and the wet filter cake is washed with pre-cooled (−15° C.) methanol (2×150 g). The wet product is dried at 50° C. under reduced pressure to obtain pure (E)-3-(4-{[2-(2-methyl-1H-indol-3-yl)-ethylamino]-methyl]-phenyl)-acrylic acid methyl ester hydrochloride salt as product. The product has usually >99 area % purity according to HPLC. IR, NMR and HR-MS confirmed the proposed structure. Melting point: decomposition starting at 251-252° C.

Example 4

Preparation of (E)-3-(4-{[2-(2-methyl-1H-indol-3-yl)-ethylamino]-methyl]-phenyl)-Acrylic Acid Methyl Ester Hydrochloride Salt 2-Methyltryptamine (50 g, 287 mmole) and (E)-3-(4-formyl-phenyl)-acrylic acid methyl ester (54.6 g, 287 mmole) are suspended in methanol (514 g). The solution is stirred for 1 hour at 20-25° C., to allow the formation of the imine intermediate. The solution is cooled to −15° C. within ca. 20 minutes. Sodium borohydride (5.43 g, 143.5 mmole) is added in several portions during ca. 1 hour while maintaining the temperature at −15° C. to −10° C. The reaction mixture is stirred for additional 30 minutes at this temperature and the temperature is raised to 20-25° C. within ca. 25 minutes. The reaction mixture is stirred for 30 minutes at 20-25° C. and water (80 g) is slowly added while maintaining the temperature at 20-25° C. The pH of the reaction mixture is adjusted to 8.5 by slow addition of an aqueous hydrochloric acid solution (ca. 37.3 g of a 21.6 m/m % solution in water) at 20-25° C., until the pH of the solution reaches 8.5. The addition needs ca. 30 minutes in this case. After completion of the addition, the reaction mixture is stirred for one hour at 20-25° C. to allow crystallization. At this stage, the solution can be seeded with crystals of (E)-3-(4-{[2-(2-methyl-1H-indol-3-yl)-ethylamino]-methyl]-phenyl)-acrylic acid methyl ester hydrochloride salt to accelerate the crystallization. A suspension is obtained. A second portion of aqueous hydrochloric acid (36 g of a 21.6% m/m HCl solution in water) is added to the suspension during 30 minutes at 20-25° C., followed by the addition of a third portion of aqueous hydrochloric acid (167.7 g of a 21.6% m/m HCl solution in water) during 30 minutes at 20-25° C. The suspension is heated to 65° C. Then, the suspension is cooled to −15° C. and stirred for 30 minutes at −10 to −15° C. to complete the crystallization. The product is isolated by filtration and the wet filter cake is washed with pre-cooled (−15° C.) methanol (2×150 g). The wet product is dried at 50° C. under reduced pressure to obtain pure (E)-3-(4-{[2-(2-methyl-1H-indol-3-yl)-ethylamino]-methyl]-phenyl)-acrylic acid methyl ester hydrochloride salt as product. The product has usually >99 area % purity according to HPLC. IR, NMR and HR-MS confirmed the proposed structure. Melting point: decomposition starting at 251-252° C.

Example 5

Preparation of 2-Methyltryptamine

Phenylhydrazine (64.92 g, 0.60 mol) and ethanol (278 g, 350 ml, 200 proof) were charged to a 2-L, round-bottomed flask. The solution was stirred under nitrogen and warmed to 35° C. The reaction was held at 35-45° C., and 5-chloro-2-pentanone (74.54 g, 0.60 mol, 97%) was added from a dropping funnel. The temperature was maintained between 35-41° C. and the addition of 5-chloro-2-pentanone completed in 30 minutes. Then the reaction was held at 35-40° C. for 30 minutes. Next, ethanol (556 g, 700 ml, 190 proof) was added to the reaction mixture. The reaction mixture was immediately warmed to reflux and held for 50 minutes. Then the reaction mixture was cooled to room temperature over 20 minutes.

The flask was then equipped for vacuum distillation. Ethanol was distilled at 35 mm Hg, in a 35-45° C. water bath to a previously provided 350 ml mark (collecting 685 g, 820 ml of distillate). Deionized water (500 g) was added to the residual solution. Distillation was continued at the same conditions to a previously provided 450 ml mark (collecting 332 g, 360 ml of distillate). Deionized water (400 g) was added to the hazy residual mixture. The mixture was cooled to less than 25° C. and the resulting mixture washed with toluene (2×347 g, 400 ml).

The product (2-methyltryptamine) was isolated by filtration. The cake was washed with toluene (130 g, 150 ml, cooled to ≦0° C.). The product was dried under vacuum at 45° C. until an LOD of <1% is obtained. The theoretical yield was 104.5 g; the actual yield was 49.2 g. While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A method of making N-hydroxy-3-[4-[[[2-(2-methyl-1H-indol-3-yl)ethyl]amino]methyl]phenyl]-2E-2-propenamide comprising:
  (a) combining 2-methyltryptamine and (E)-3-(4-formyl-phenyl)-acrylic acid methyl ester to form an admixture;
  (b) stirring the admixture;
  (c) cooling the admixture;
  (d) reducing the admixture;
  (e) adding hydrochloric acid to the admixture to form the (E)-3-(4-{[2-(2-methyl-1H-indol-3-yl)-ethylamino]-methyl]-phenyl)-acrylic acid methyl ester hydrochloride salt;
  (f) combining sodium hydroxide and (E)-3-(4-{[2-(2-methyl-1H-indol-3-yl)-ethylamino]-methyl]-phenyl)- acrylic acid methyl ester hydrochloride salt to form an admixture at a temperature of less than about −10° C.; and subsequently (g) adding hydroxylamine to the admixture to form the N-hydroxy-3-[4-[[[2-(2-methyl-1H-indol-3-yl)ethyl]amino]methyl]phenyl]-2E-2-propenamide.

2. The method of claim 1, wherein the (b) stirring occurs at a temperature range of from about 20° C. to about 25° C.

3. The method of claim 1, wherein the admixture is cooled in (c) to a temperature of about −15° C.

4. The method of claim 1, wherein reducing (d) is by the addition of sodium borohydride to the admixture.

5. The method of claim 4, wherein the sodium borohydride is added while the temperature is maintained at a range from about −15° C. to about −10° C.

6. The method of claim 1, wherein the temperature of (f) is less than about −15° C.

7. The method of claim 1, wherein the hydroxylamine is used in an amount ranging from about 4 to about 13 equivalents.

* * * * *